United States Patent [19]

Muramatsu et al.

[11] Patent Number: 5,211,054
[45] Date of Patent: May 18, 1993

[54] METHOD AND SYSTEM FOR ANALYZING A GELATION REACTION BY UTILIZING A PIEZOELECTRIC RESONATOR

[75] Inventors: Hiroshi Muramatsu, Tokyo; Isao Karube, Kawasaki, both of Japan

[73] Assignee: Seiko Instruments Inc., Japan

[21] Appl. No.: 767,532

[22] Filed: Sep. 26, 1991

Related U.S. Application Data

[63] Continuation of Ser. No. 234,305, Aug. 9, 1988, abandoned.

[30] Foreign Application Priority Data

| Aug. 19, 1987 | [JP] | Japan | 62-205747 |
| Aug. 19, 1987 | [JP] | Japan | 62-205748 |
| Aug. 19, 1987 | [JP] | Japan | 62-205749 |
| Aug. 27, 1987 | [JP] | Japan | 62-213591 |
| May 10, 1988 | [JP] | Japan | 63-112961 |

[51] Int. Cl.$^5$ .................................................. G01N 11/16
[52] U.S. Cl. .................................... 73/64.42; 73/54.25
[58] Field of Search ............... 73/54, 59, 64.1, 32 A, 73/579, 54.01, 54.24, 54.25, 64.42, 64.41

[56] References Cited

U.S. PATENT DOCUMENTS

| 3,903,732 | 9/1975 | Rork et al. | 73/54 |
| 4,695,956 | 9/1987 | LeVeen et al. | 73/54 |
| 4,741,200 | 5/1988 | Hammerle | 73/54 |
| 4,783,987 | 11/1988 | Hager et al. | 73/54 |
| 4,799,378 | 1/1989 | Portman, Jr. et al. | 73/54 |
| 4,811,593 | 3/1989 | Miura et al. | 73/54 |
| 4,862,384 | 8/1989 | Bujard | 73/54 |

FOREIGN PATENT DOCUMENTS

| 0214366 | 3/1987 | European Pat. Off. |
| 1484967 | 6/1967 | France. |
| 2535346 | 5/1984 | France. |
| 851621 | 10/1960 | United Kingdom. |
| 1086236 | 10/1967 | United Kingdom. |
| 2004376 | 3/1979 | United Kingdom. |
| 2124767 | 2/1984 | United Kingdom. |
| 2130723 | 6/1984 | United Kingdom. |

Primary Examiner—Hezron E. Williams
Assistant Examiner—Michael Brock
Attorney, Agent, or Firm—Bruce L. Adams; Van C. Wilks

[57] ABSTRACT

A viscosity measuring system comprises a cell containing gelable liquid and a piezoelectric resonator mounted in the cell. The piezoelectric resonator has a prescribed characteristic, such as electrical resistance or resonant frequency, which varies in accordance with the gelating of the liquid. Solid particles suspended in the liquid are deposited on the piezoelectric resonator during gelating of the liquid to amplify the prescribed resonator characteristic. A measuring circuit measures the variation of the resonator characteristic to thereby determine the gelation time of the liquid.

21 Claims, 14 Drawing Sheets

METHOD AND SYSTEM FOR ANALYZING A GELATION REACTION BY UTILIZING A PIEZOELECTRIC RESONATOR

This is a continuation application of parent application Ser. No. 234,305 filed Aug. 19, 1988, abandoned.

BACKGROUND OF THE INVENTION

1. Field of the Invention

The present invention relates to a system for measuring a viscosity of a gelable liquid in the fields of chemistry, physical chemistry, biochemistry, foodstuffs, medical services and the chemical industry. The viscosity measuring system utilizes a piezoelectric resonator for monitoring a viscosity change of a gelable liquid.

2. Description of Prior art

A capillary method, a rotational method, a falling ball method, and the like, have primarily been employed conventionally to measure a viscosity. The capillary method measures the viscosity of a liquid sample from its falling speed in a capillary and the falling ball method places a metal ball into a liquid sample and determines the viscosity from its falling speed. The rotational method rotates a cylindrical metal rod inside the sample liquid and determines the viscosity by measuring its shear stress.

The conventional viscosity measuring methods involve the problem that measurement is not possible for a limited amount of a sample. The capillary method and the falling ball methods are not free from the problem that a long measuring time and a great deal of labor are necessary for the measurement. Since the measurement is carried out by a mechanical system in accordance with the rotational method, this method involves the problems that the measurement is likely to be affected by external influences such as of vibration and maintenance of devices is also necessary.

Furthermore, in order to measure a gelation reaction, particularly a gelation reaction in the analysis of a blood coagulation system, a method which measures optically turbidity of a sample and a method which applies mechanical vibration and detects a viscoelastic change due to gelation have been employed conventionally.

The conventional method which measures turbidity involves the drawbacks that measurement of a colored sample cannot be made and since an optical measuring system is included, its system construction becomes complicated. On the other hand, the optical method is not said to be a correct method because it does not directly measure gelation. The method which applies mechanical vibration is not free from the problems that occur due to the presence of mechanical portions also, the system becomes complicated and trouble is likely to occur. The gelation reaction is likely to be impeded by mechanical vibration and there is a limit to the accuracy measurement by this method. In addition to these problems, all of the methods described above involve in common the problem that at least about 0.2 ml of sample is necessary.

Moreover, a viscosity measuring method by use of a torsionally vibrating crystal has also been developed.

In the case of the measuring method using the torsionally vibrating crystal, a certain amount of sample is necessary and the viscosity cannot be measured in an electrolytic solution.

Furthermore, no reports have been known in the past about the measurement of the viscosity change by use of a crystal.

SUMMARY OF THE INVENTION

It is the primary object of the present invention to provide a chemical analyzer, by which the above-mentioned defects of the conventional techniques are overcome and employs an entirely novel viscosity measuring system which uses a piezoelectric resonator.

In accordance with the present invention, there is provided a viscosity measuring system comprising a piezoelectric resonator for detecting the viscosity of a gelable liquid, and measuring means connected to the piezoelectric resonator for measuring an index of the liquid. The piezoelectric resonator defects the viscosity of the liquid by measuring a resonant frequency shift of the resonator or a resistance included in an equivalent circuit of the resonator during gelating of the liquid.

DESCRIPTION OF THE PREFERRED EMBODIMENTS

Figure 1A:
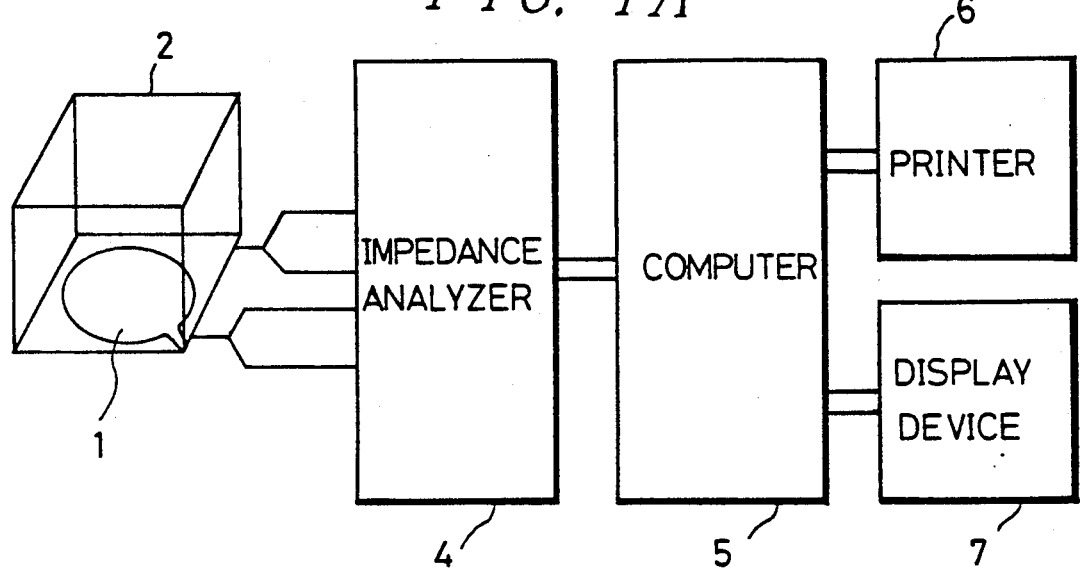
FIGS. 1A and 1B are schematic views of a viscosity measuring system in accordance with the present invention.

According to the present invention, a resonant frequency shift which indicates the shift from resonant frequency measured in air or a resistance included in equivalent circuit of the piezoelectric resonator is used as an index of viscosity of the liquid The measuring system is also a chemical reaction measuring system which brings a liquid into contact with one or both sides of the piezoelectric resonator, traces a chemical reaction involving the change of viscoelasticity of the resonator by determining the resonant frequency of the resonator or an equivalent resistance, and measures the concentration of chemical substances by utilizing the tracing result.

The present invention will now be described in detail with reference to the following examples.

I. Viscosity measuring system

The present invention enables the viscosity measurement of a liquid This is achieved by the measuring system which comprises a piezoelectric resonator and measuring means connected to the piezoelectric resonator for measuring an index of the viscosity of the liquid The index is either a resonant frequency shift or a resistance value included in equivalent circuit of the resonator.

EXAMPLE 1

The viscosity measuring system in accordance with the present example is a system for measuring the viscosity of a liquid by bringing a liquid into contact with one, or both, of two electrodes of a piezoelectric resonator, measuring the resonant frequency and determining its difference from the resonant frequency in air. This viscosity measuring system comprises a piezoelectric crystal, a cell for holding the liquid on the surface of the piezoelectric crystal, a measuring circuit for measuring the impedance at frequencies near the resonant frequency of the piezoelectric crystal, a calculation unit for calculating the resonant frequency from the measured data and a data display/recording device This system makes it possible to measure the viscosity of even a small amount of a liquid sample within a short period and with a high level of accuracy.

Viscosity measurement by the present system is carried out in the following sequence.

First, a liquid sample is placed into a cell and is brought into contact with the piezoelectric crystal. The impedance of this piezoelectric crystal is measured within a frequency range on both sides of the resonant frequency. At this time, if conductance and susceptance as the real and imaginary components of the admittance which is the inverse value of the impedance are plotted on X - Y axes, they describe a circle. When the center of this circle is determined by the least square method, the susceptance has the value which is in agreement with the susceptance value at this center at the frequency at which conductance reaches the maximum. Therefore, the resonant frequency can be determined by approximation to a polynominal equation of the susceptance and the measuring frequency. Assuming that the difference of the resonant frequency at this time from the resonant frequency in air is $\Delta F$, this value has a linear relationship with $\sqrt{\rho\eta}$ ($\rho$: density, $\eta$: viscosity) so that the viscosity can be determined by utilizing this relationship.

Properties of the piezoelectric resonator and the operation of the resonator in the present analyzer are illustrated as follows A piezoelectric resonator such as quartz resonator is a device which utilizes a piezoelectric property. When a voltage of a frequency near the resonant frequency is applied, the piezoelectric resonator causes mechanical vibration. Though this vibration is extremely small, shear stress develope between the liquid and the surface of the piezoelectric resonator under the condition that the piezoelectric crystal is in contact with the liquid. Since this force is believed to be in equilibrium with the force of the piezoelectric crystal vibrating as an elastic material, the difference $\Delta F$ of the resonant frequency when no liquid exists and when the piezoelectric crystal is in contact with the liquid if it existed is revealed to correspond to $\sqrt{\rho\eta}$. Therefore, $\sqrt{\rho\eta}$ the sample liquid can be determined from the working curve that is determined in advance, by determining this $\Delta F$ value.

Figure 1B:
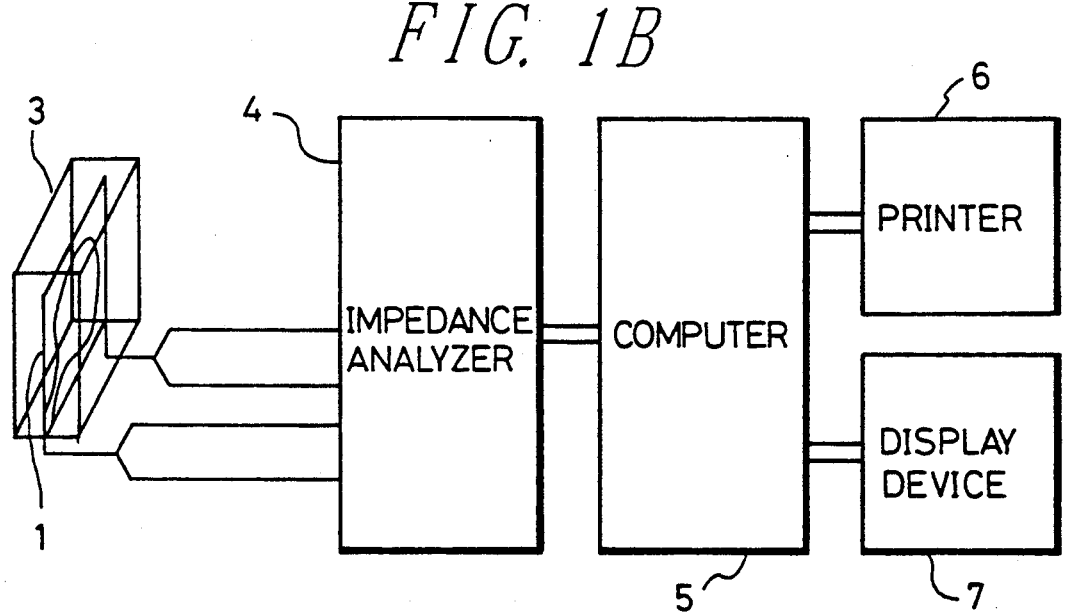

FIGS. 1A and 1B show schematically the viscosity measuring system in accordance with the present invention. In FIG. 1A, the piezoelectric crystal 1 is fixed to a cell 2 on side thereof and the other side of the piezoelectric crystal 1 is brought into contact with a liquid or mounted in a cell 3 in which both sides are brought into the liquid as shown in FIG. 1B, and is connected to an impedance analyzer 4 to which an arbitrarily measuring frequency can be set. The impedance analyzer 4 is connected to a computer 5 for calculation or control, and a printer 6 and a display 7 are connected to the computer 5.

Measurement is carried out by placing the liquid sample into the cell and measuring the impedance around the resonant frequency of the piezoelectric resonator. More definitely, the impedance is measured in the following way. Since the resonant frequency exists between the frequencies that provide the maximum and minimum values of the susceptance as the imaginary number of the admittance, the maximum and minimum values of the susceptance are determined by frequency scanning and the conductance and the susceptance are measured by equidistant frequencies between these frequencies. The data of the conductance and susceptance are processed by the least square method of the circle to obtain the center of this circle, and the frequency on such a circle that exhibits the same susceptance value as the susceptance value at the center is obtained from approximation to a polynominal equation of the susceptance and the measuring frequency so that the frequency thus obtained is used as the resonant frequency. The difference between this resonant frequency and the resonant frequency that is obtained in the same way but when no liquid exists is used as $\Delta F$.

Figure 2:
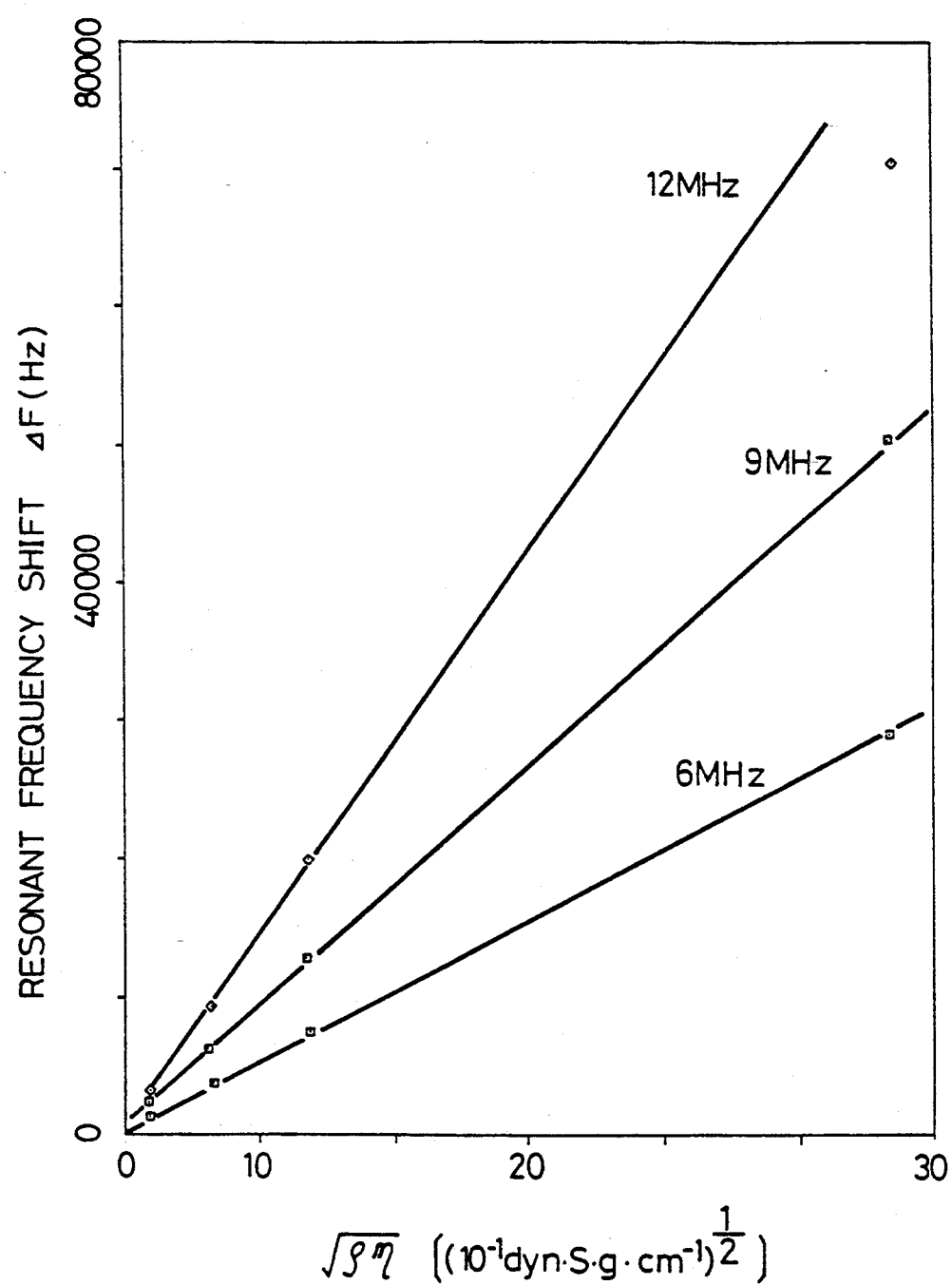
FIG. 2 is an explanatory view showing the relationship between $\Delta F$ and $\sqrt{\rho\eta}$ of the water-glycerol mixture measured by the viscosity measuring system of the present invention.

The frequency change $\Delta F$ was determined for each of water-glycerol mixture ranging from 100% water to 100% glycerol using 6 MHz, 9 MHz and 12 MHz AT cut piezoelectric crystals and using the cell of the type shown in FIG. 1A wherein one of the sides of the piezoelectric crystal was in contact with the liquid, at 25° C. The results are shown in FIG. 2. As shown in FIG. 2, it could be understood that a linear relationship exists between $\Delta F$ and $\Delta\sqrt{\eta}$.

When automatic setting was made by a computer within the impedance measurement range in the system of the present invention, it has been clarified that the resonant frequency could be calculated within one minute for both the impedance measurement and the calculation time.

When the amount of the sample liquid was changed, the change of $\Delta F$ was extremely small and was negligible In the case of the cell shown in FIG. 1A, it was demonstrated that the measurement could be carried out sufficiently even when the amount of the sample liquid was below 0.1 ml.

Furthermore, measurement could be carried out by directly immersing the piezoelectric crystal into the liquid without using the cell.

When the measuring voltage was 0.01 V, 0.1 V and 1 V, respectively, it was found that ΔF was not dependent on the measuring voltage.

The resonant frequency can be measured by determining such a frequency at which the absolute value of the impedance or the resistance as the real number component becomes minimal, but the method demonstrated in the embodiment described above can provide more accurate results because such a method is susceptible to a measurement error or to the influences of a parallel capacitor in the equivalent circuit of the piezoelectric crystal.

EXAMPLE 2

The viscosity measuring system in accordance with the present example is a system for measuring the viscosity of a liquid by bringing a liquid into contact with one, or both, of two electrodes of a piezoelectric crystal, measuring the resonant frequency and determining its difference from the resonant frequency of air in order to determine the viscosity of the liquid. This viscosity measuring system consists of a piezoelectric crystal, a cell for holding the liquid on the surface of the piezoelectric resonator, an oscillation circuit, a frequency measuring device, a data monitor device and a recording/display device. Viscosity measurement by the present system is carried out in the following sequence First, a liquid sample is placed into a cell and is brought into contact with the piezoelectric crystal so as to measure the oscillation frequency. The difference of this oscillation frequency from that in air is called ΔF. Since this ΔF value has a linear relationship with $\sqrt{\rho\eta}$ ($\rho$: density, $\eta$: viscosity), viscosity is measured by utilizing this relationship.

Figure 3A:
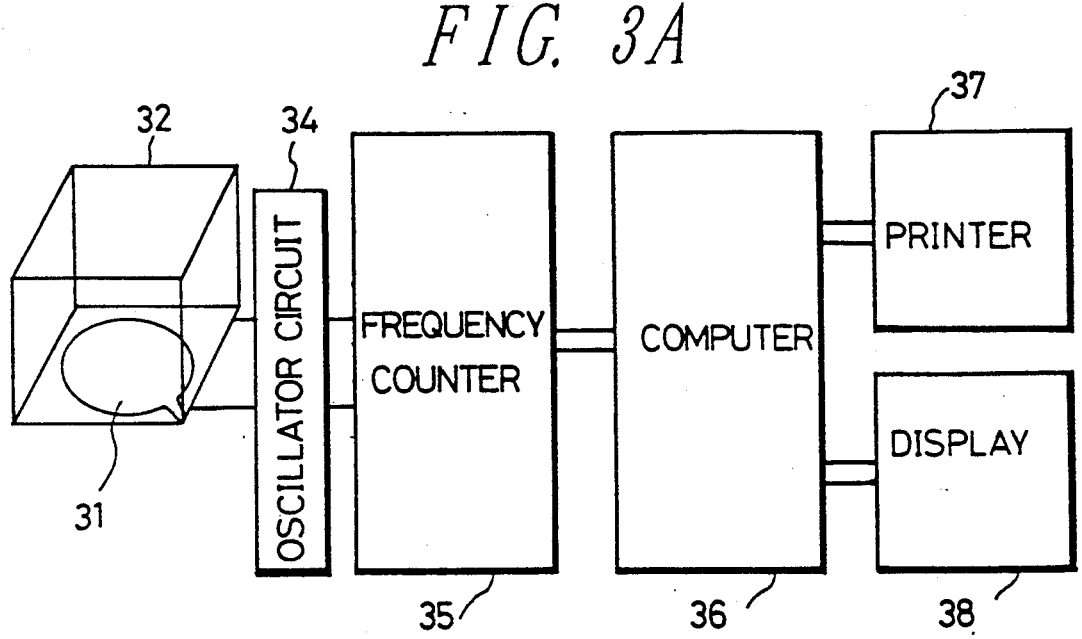
FIG. 3A and 3B are schematic views of a viscosity measuring system in accordance with the present invention.
Figure 3B:
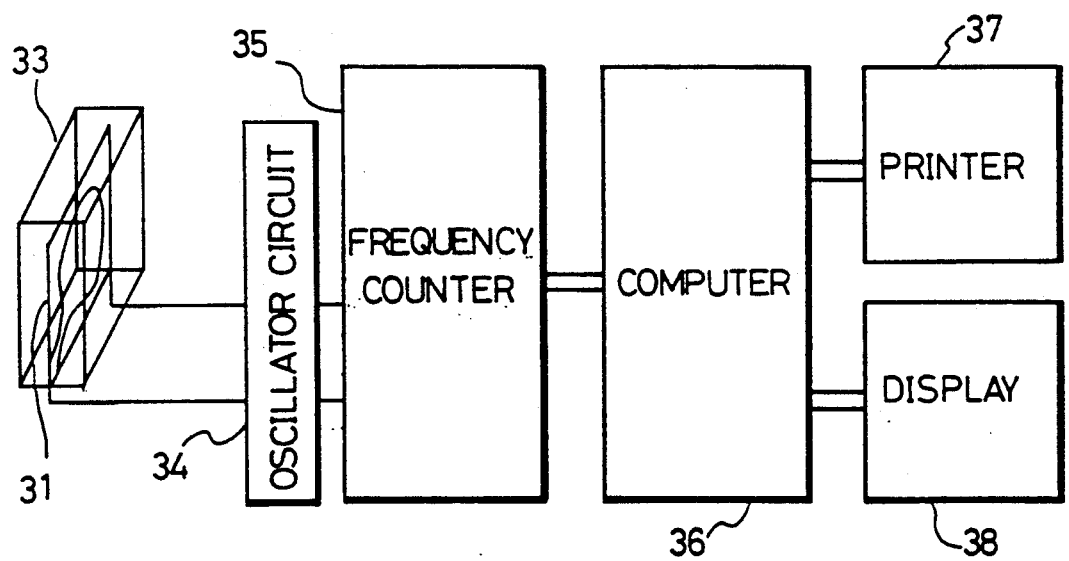

FIGS. 3A and 3B show schematically the viscosity measuring system in accordance with other embodiments of the present invention. In FIG. 3A, the piezoelectric resonator 31 is fixed to a cell 32 on one side thereof and the other side of the piezoelectric resonator 31 is brought into contact with a liquid or mounted in a cell 33 in which both sides are brought into contact with the liquid as shown in FIG. 3B, and is connected to an oscillation circuit 34. The oscillation circuit 34 is connected to a frequency counter 35 and further to a computer 36 for monitoring data. A printer 37 and a display 38 are connected to the computer 36.

Measurement was carried out by placing a liquid sample into the cell, measuring the oscillation frequency and obtaining the difference ΔF between this oscillation frequency and the oscillation frequency determined when no liquid existed.

Figure 4:
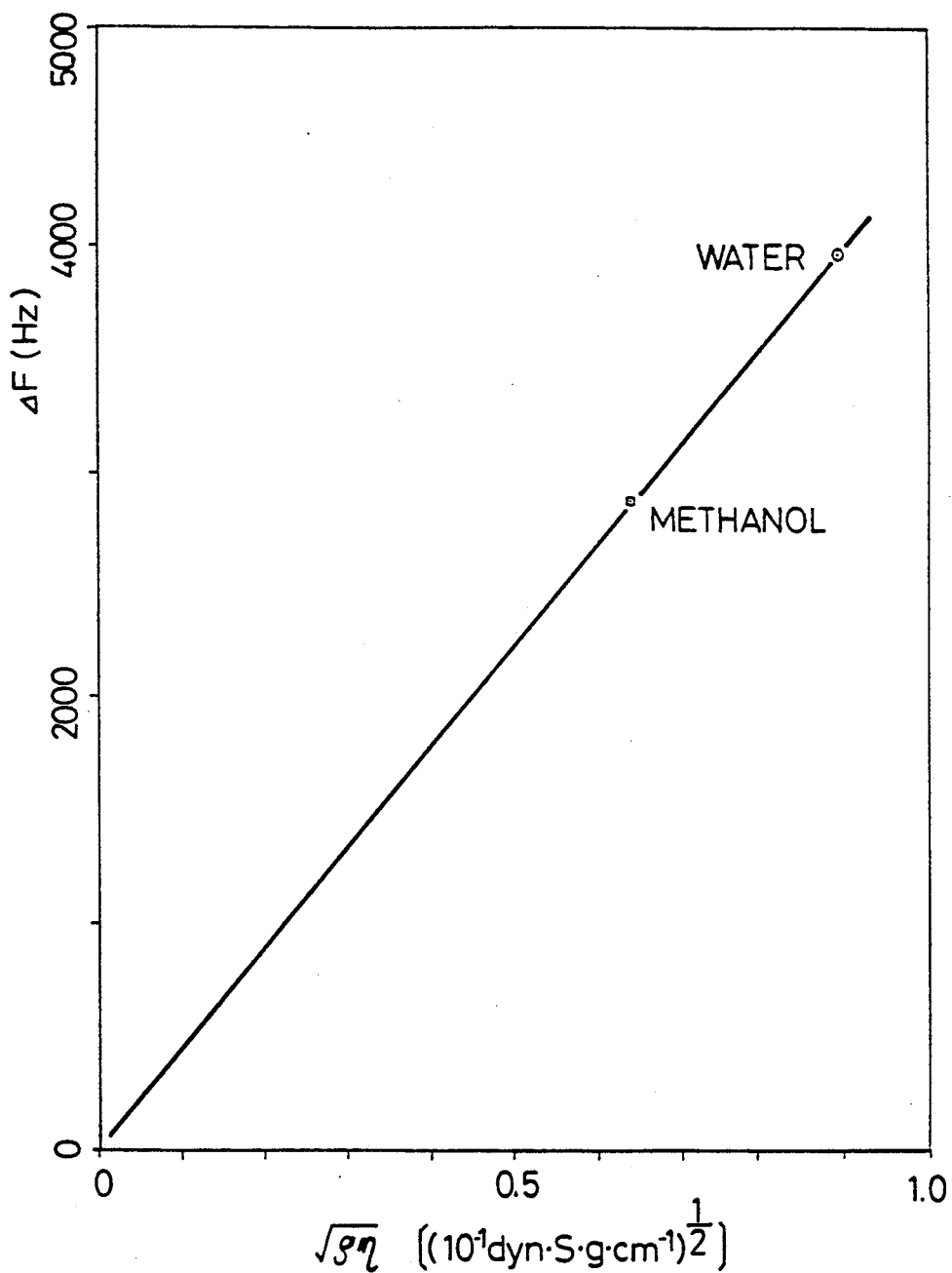
FIG. 4 is an explanatory view showing the relationship between $\Delta F$ and $\Delta\sqrt{\eta}$ of the water-methanol mixture measured by the viscosity measuring system of the present invention.

The frequency change was determined by using a 9 MHz AT cut piezoelectric crystal and the cell of the type shown in FIG. 3A wherein one of the sides of the crystal was in contact with the liquid, at 30° C. for a water-methanol mixture. The results are shown in FIG. 4. As shown in FIG. 4, it could be understood that a linear relationship exists between ΔF and Δ$\sqrt{\eta}$.

When the amount of the sample liquid was changed, the change of ΔF was extremely small and was negligible. In the case of the cell shown in FIG. 3A, it was demonstrated that the measurement could be carried out sufficiently even when the amount of the sample liquid was below 0.1 ml.

Furthermore, measurement could be carried out by directly immersing the piezoelectric crystal into the liquid without using the cell.

EXAMPLE 3

Figure 5:
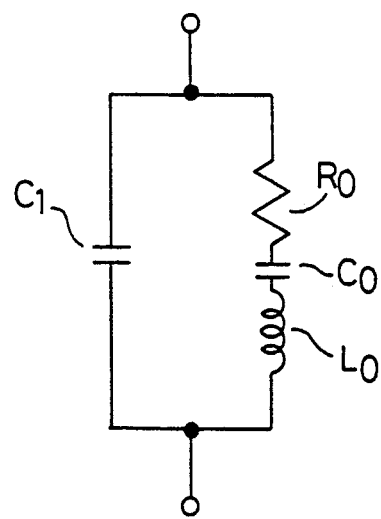
FIG. 5 is an equivalent circuit diagram of a piezoelectric resonator.

The viscosity measuring system in accordance with the present example brings a liquid into contact with one or both of its two electrodes and determines the viscosity of the liquid by determining the value of the resistance component among an inductance Lo, a capacitance Co and a resistance Ro connected in series with one another in equivalent circuit constants of a piezoelectric crystal see FIG. 5. This viscosity measuring system comprises the piezoelectric crystal, a cell for holding a liquid on the surface of the piezoelectric resonator, a measuring circuit for measuring an impedance at a frequency around the resonant frequency of the piezoelectric crystal, a calculation unit for calculating the equivalent circuit constants from the measured data and a data display/recording device. The viscosity measuring system of the present invention makes it possible to measure the viscosity of even a small amount of a liquid sample within a short periods of time and with a high level of accuracy.

Viscosity measurement by the present system is carried out in the following sequence.

First, a liquid sample is placed into a cell and is brought into contact with the piezoelectric crystal. The impedance of this piezoelectric crystal is measured within a frequency range on both sides of the resonant frequency. At this time, if conductance and susceptance as the real and imaginary components of the admittance which is the inverse number of the impedance are plotted on X - Y axes, they describe a circle. The value of the resistance Ro (referred to as "deficit resistance") in the equivalent circuit of the piezoelectric crystal shown in FIG. 5 can be obtained by determining the diameter of this circle by the least square method and then obtaining its inverse number. Since $\sqrt{\rho\eta}$ ($\rho$: density, $\eta$: viscosity) exhibits a linear relationship, the viscosity can be determined by utilizing this relationship.

Properties of the piezoelectric resonator and the operation of the resonator in the present analyzer are illustrated as follows.

A piezoelectric resonator such as quartz resonator is a device which utilizes a piezoelectric property. When a voltage of a frequency near the resonant frequency is applied, the piezoelectric resonator cause mechanical vibration. Under the state where the piezoelectric resonator is in contact with a liquid, resistance force acts between the liquid and the surface of the piezoelectric resonator, though this vibration is extremely small. If the mechanical vibration of the piezoelectric resonator is considered in association with its electrical vibration, the resistance coefficient of this mechanical resistance can be considered in association with the electrical resistance. Therefore, the resistance Ro is believed to be a value which reflects the friction factor on the surface of the piezoelectric crystal and the $\sqrt{\rho\eta}$ of the sample liquid can be determined from the working curve that is determined in advance.

The viscosity measuring system in accordance with the present example is used the same system as shown in FIGS. 1A and 1B.

Measurement is carried out by placing the liquid sample into the cell and measuring the impedance around the resonant frequency of the piezoelectric crystal. More definitely, the impedance is measured in the following way. Since the resonant frequency exists between the maximum and minimum values of the susceptance as the imaginary number of the admittance, the maximum and minimum values of the susceptance are determined by frequency scanning and the conductance and the susceptance are measured by equidistant frequencies between these frequencies. The data of the conductance and susceptance are processed by the least square method of the circle to obtain the diameter of the circle, and its inverse number is used as the Ro value.

Measurement of water-glycerol mixture

Figure 6:
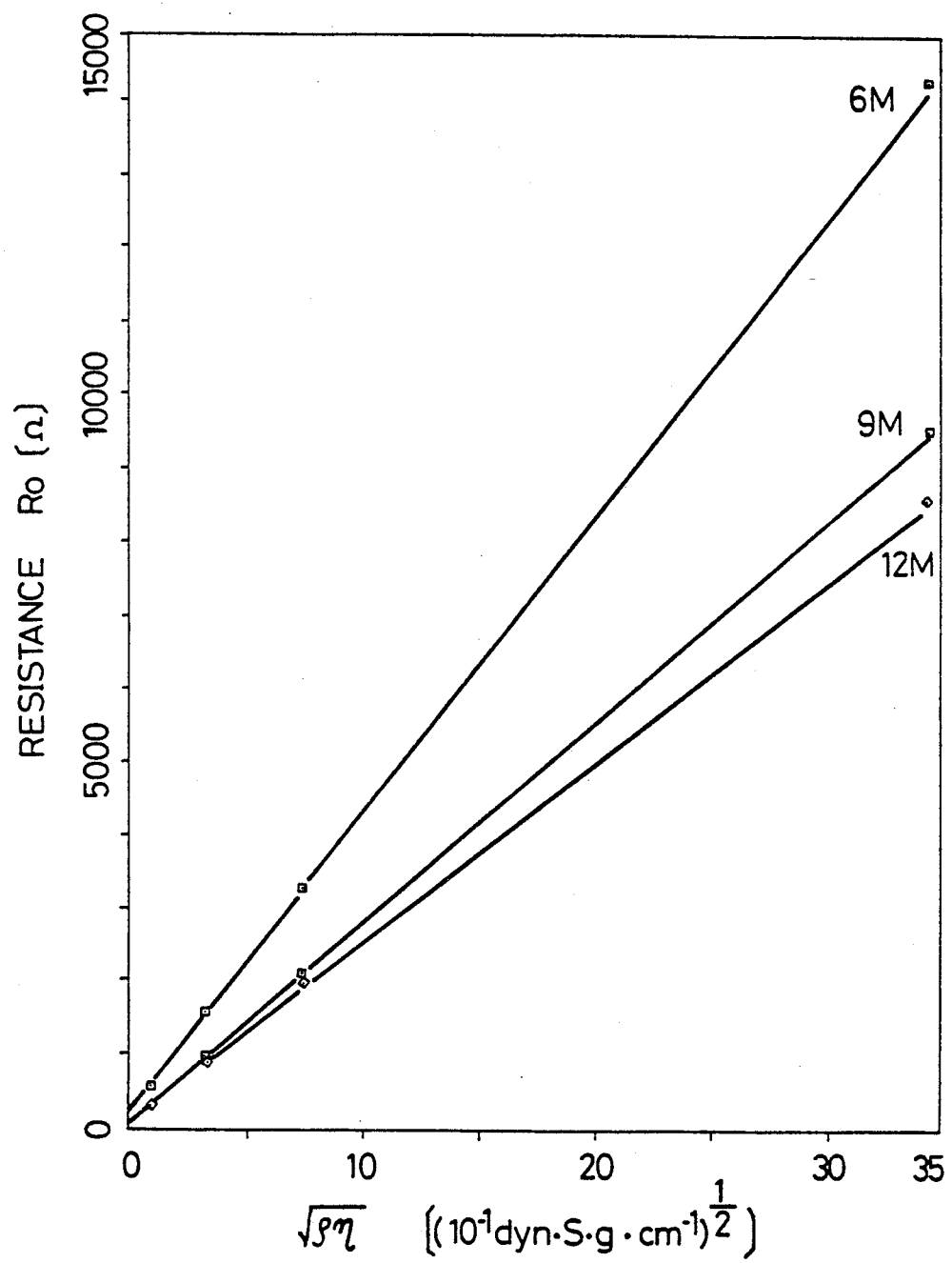
FIG. 6 is an explanatory view showing the relationship between a resistance Ro and $\sqrt{\rho\eta}$ of a water-glycerol mixture measured by the viscosity measuring system of the present invention.

The resistance value Ro was determined for each of water-glycerol mixture ranging from 100% water to 100% glycerol using 6 MHz, 9 MHz and 12 MHz AT cut piezoelectric crystals whose surfaces were plated with palladium and using the cell of the type shown in FIG. 1A wherein one of the sides of the piezoelectric crystal came into contact with the liquid, at 25° C. The results are shown in FIG. 6. As shown in FIG. 6, it could be understood that an extremely high linear relationship exists between Ro and $\sqrt{\rho\eta}$.

Measurement of water-ethanol mixture

Figure 7:
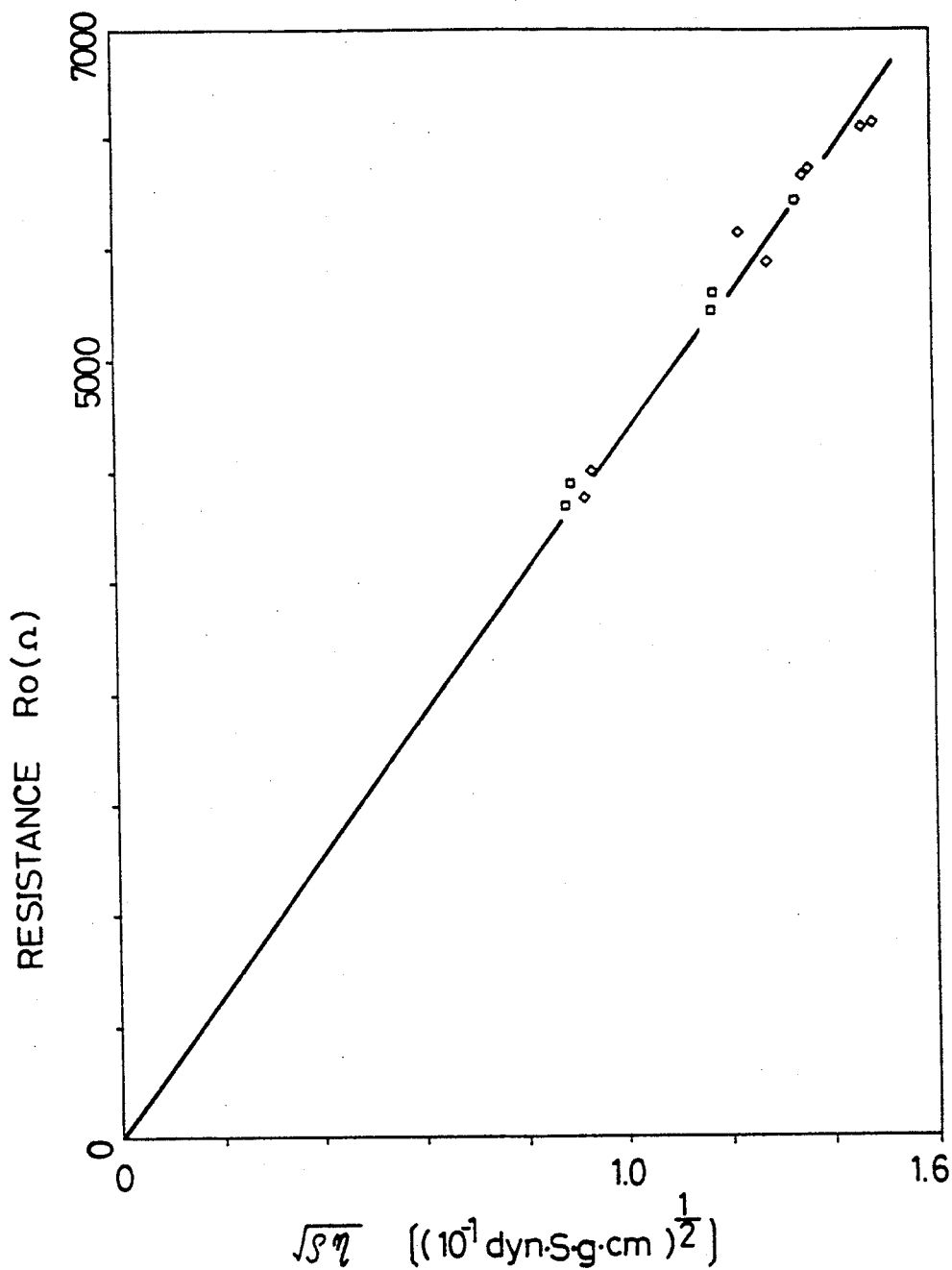
FIG. 7 is an explanatory view showing the relationship between the resistance Ro and $\sqrt{\rho\eta}$ of a water-ethanol mixture measured by the viscosity measuring system of the present invention.

The resistance value Ro was determined for each of water-ethanol mixture ranging from 100% water to 100% ethanol using a 9 MHz AT cut piezoelectric crystal and using the cell of the type shown in FIG. 1B wherein both sides of the piezoelectric resonator came into contact with the liquid, at 25° C. and 30° C. The results are shown in FIG. 7. As demonstrated in FIG. 7, it could be understood that a linear relationship exists between Ro and $\sqrt{\rho\eta}$ and is hardly affected by temperatures.

If automatic setting is made by a computer within the impedance measurement range in the system of the present invention, it has been clarified that Ro can be calculated within one minute for both the impedance measurement and the calculation time.

When the amount of the sample liquid was changed, the change of Ro was extremely small and was negligible. In the case of the cell shown in FIG. 1A, it was demonstrated that the measurement could be carried out sufficiently even when the amount of the sample liquid was below 0.1 ml.

Furthermore, measurement could be carried out by directly immersing the piezoelectric crystal into the liquid without using the cell.

When the measuring voltage was 0.01 V, 0.1 V and 1 V, respectively, the value was obtained in accordance with these measuring voltages.

Though Ro can be determined by determining the deficit resistance itself at the resonant frequency, the method demonstrated in the embodiment described above can provide more accurate results because the offset of the measuring system and the influence of the parallel capacitor $C_1$ exist.

II. Chemical reaction measuring system

The chemical reaction measuring system of the present invention is a system which brings a liquid into contact with one or both sides of an AT cut piezoelectric resonator, traces a chemical reaction involving the change of viscoelasticity by determining the change of the resonant frequency of the piezoelectric resonator or a deficit resistance, and measures the concentration of chemical substances by utilizing the tracing result.

The present invention comprises at least a resonant frequency measuring circuit or a deficit resistance measuring circuit, besides an AT cut piezoelectric crystal.

The chemical reaction measuring system in accordance with the present invention uses an AT cut piezoelectric crystal, for example, as a detector and measures continuously the deficit resistance of the piezoelectric crystal or the change of its resonant frequency, thereby making it possible to measure a chemical reaction, particularly a gelation reaction.

Properties of the piezoelectric resonator and the operation of the resonator in the present analyzer are illustrated as follows.

A piezoelectric resonator such as quartz resonator is a device which utilizes a piezoelectric property. When a voltage of a frequency near its resonant frequency is applied, the piezoelectric resonator causes mechanical vibration. This vibration receives resistance, though extremely small, due to shear stress between a liquid and the surface of the piezoelectric resonator under the state where the piezoelectric resonator is in contact with the liquid. The resistance coefficient of this mechanical resistance can be considered in association with electrical resistance when the mechanical vibration of the piezoelectric crystal is considered in association with electrical vibration. Therefore, the deficit resistance at the resonant frequency is believed to be a value that reflects the friction factor on the surface of the piezoelectric resonator, and the change of viscosity with the chemical reaction can be traced by measuring continuously this deficit resistance. Since the shear stress of the piezoelectric crystal is in equilibrium with the force of vibration of the piezoelectric crystal as an elastic material, the change of the resonant frequency corresponds to the viscosity change. Therefore, the viscosity change with the chemical reaction can be traced by measuring continuously the frequency change.

EXAMPLE 4

The viscosity measuring system used in the present example is the same system as shown in FIGS. 1A and 1B.

Measurement is carried out by placing a sample liquid into the cell and measuring the impedance near the resonant frequency of the piezoelectric crystal. More definitely, since the resonant frequency exists between the frequencies that provide the maximum and minimum values of the susceptance which is the imaginary number component of admittance, the maximum and minimum values of susceptance are determined by frequency scanning and conductance and susceptance are measured at equidistant frequencies between these frequencies. The data of the conductance and susceptance are processed by the least square method of a circle and its inverse number is used as the value of the deficit resistance. The center of the circle is also determined and the frequency on such a circle that provides the same susceptance value as the susceptance value at the center is obtained from approximation to a polynominal equation of the susceptance and the measuring frequency. The difference between this resonant frequency and the resonant frequency obtained when no liquid exists is used as $\Delta F$.

Such measuring and calculation processings can be carried out automatically by the computer and in the measuring system of the present invention, a series of operations can be carried out within one minute.

Application to endotoxin analysis

Endotoxin concentration was determined by the gelation of Limulus Amebocyte Lysate (LAS) using this measuring system.

Figure 8A:
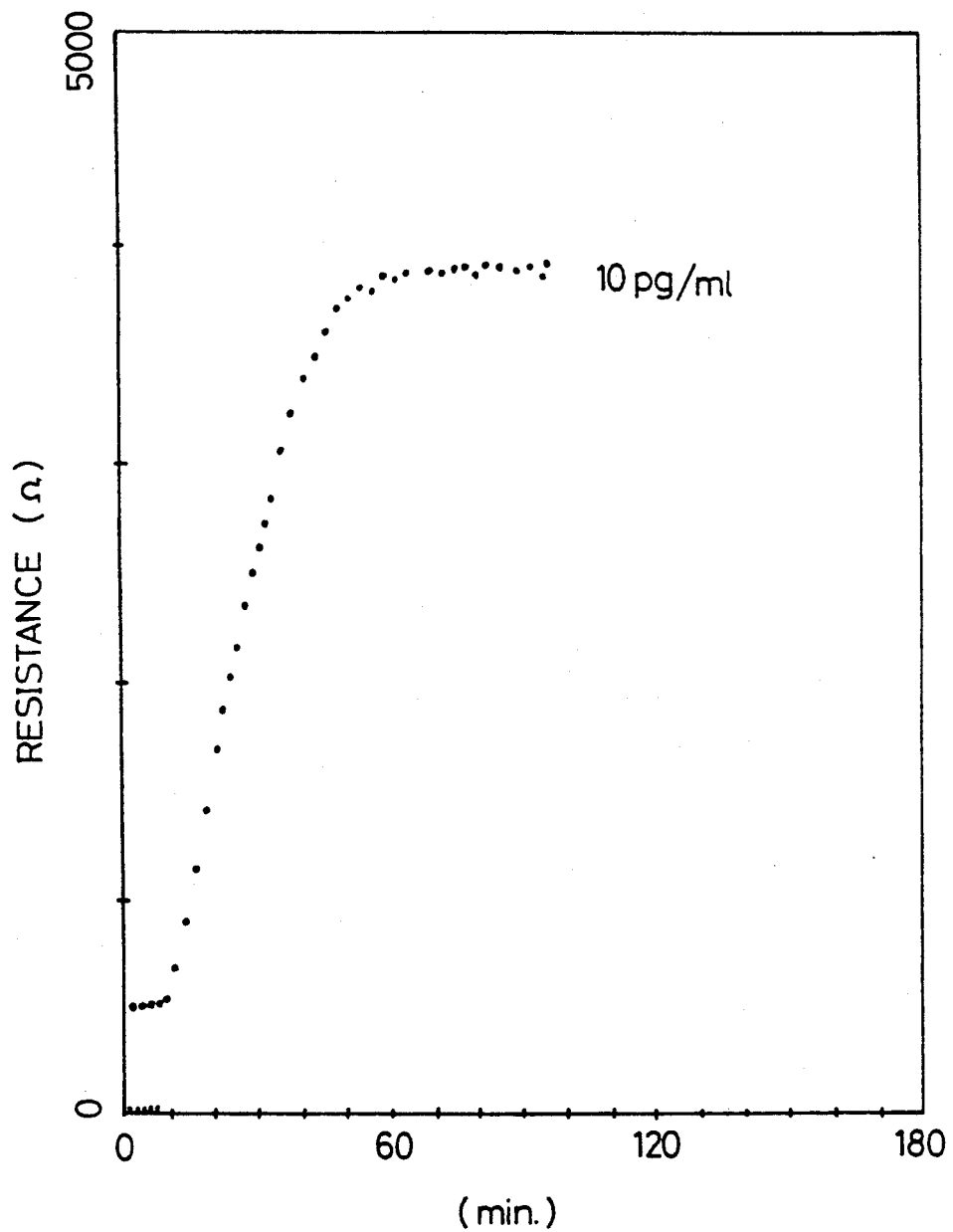
FIG. 8A shows a deficit resistance with respect to a reaction time.
Figure 8B:
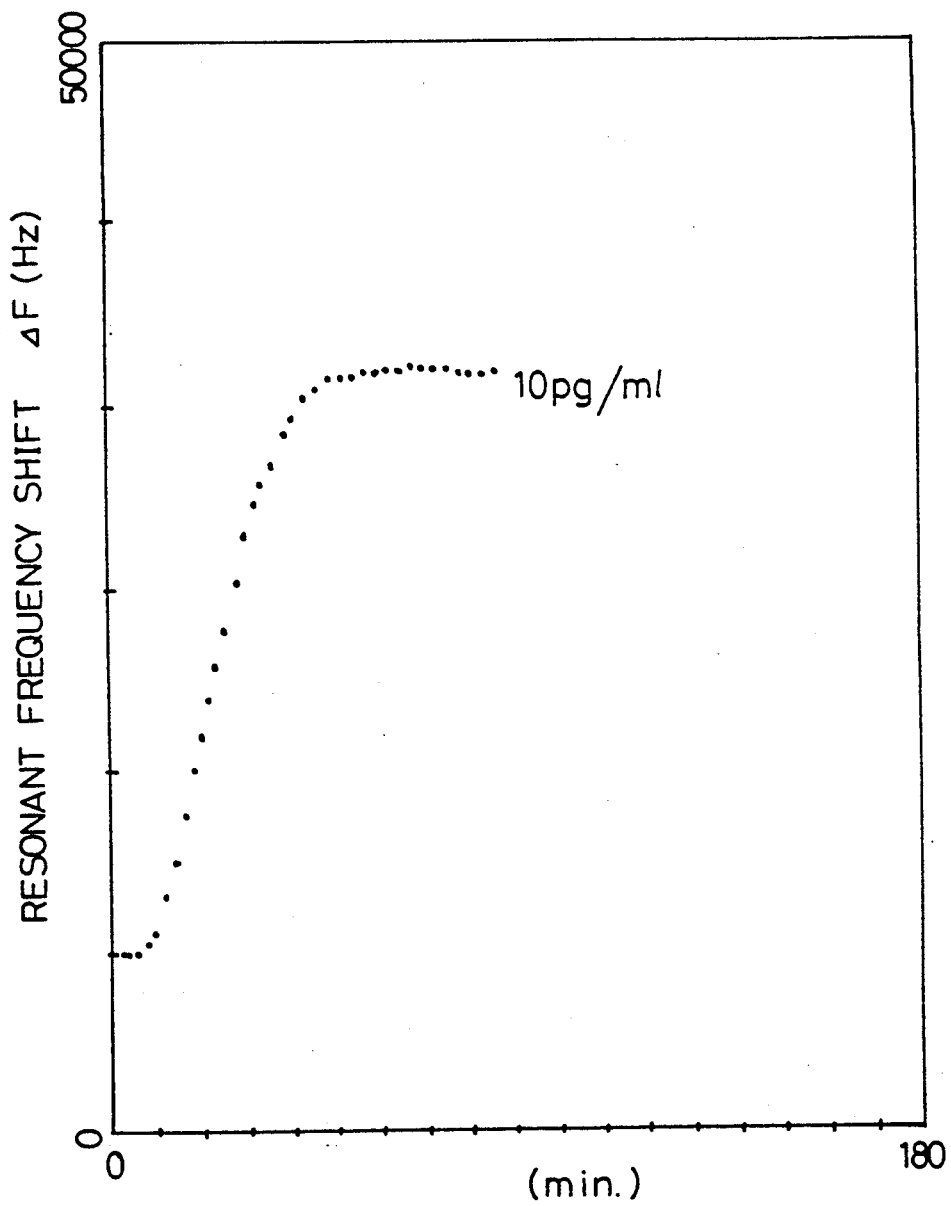
FIG. 8B shows a resonant frequency change with respect to the reaction time.
Figure 9:
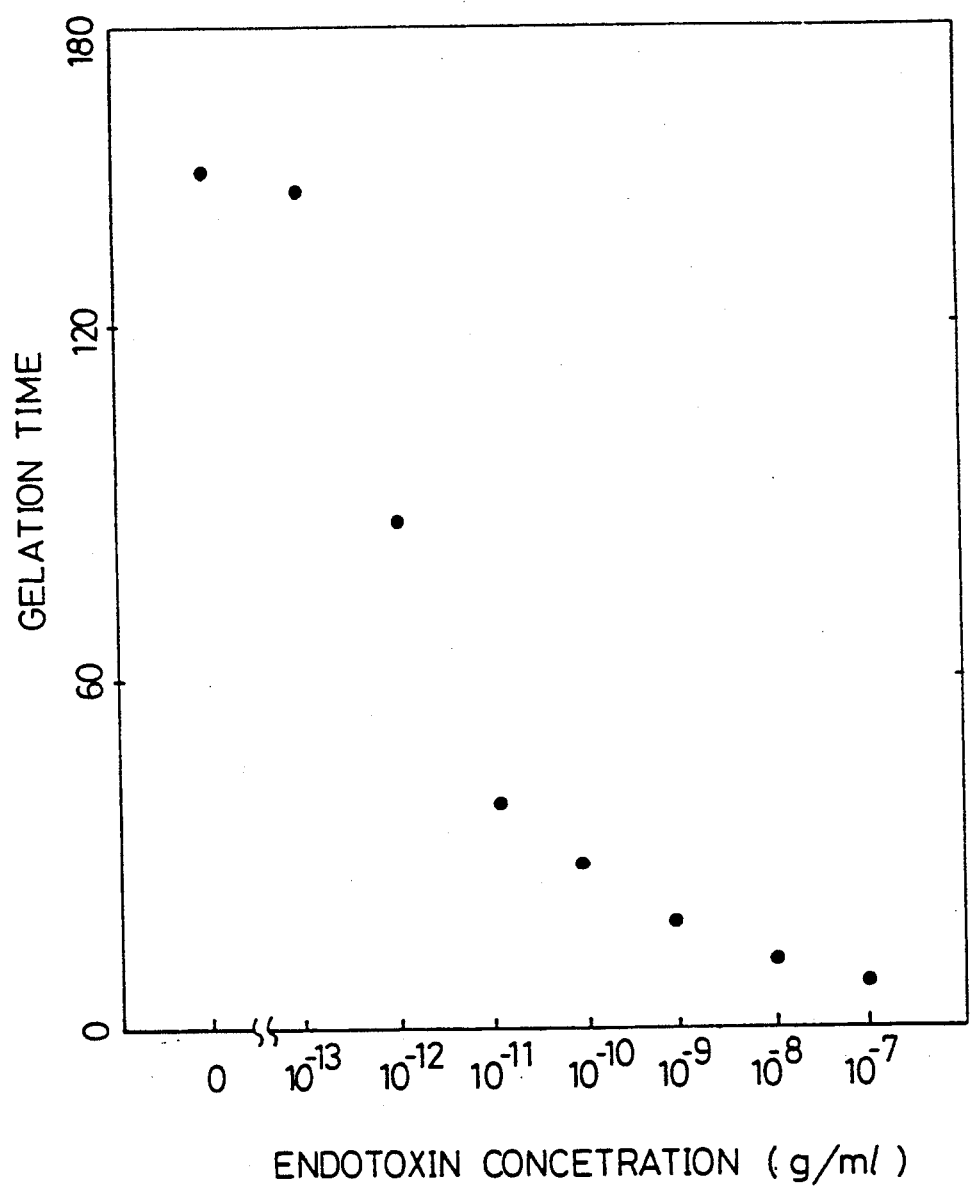
FIG. 9 shows the relationship between an endotoxin concentration and a gelation time.

After 0.2 ml of a sample liquid and a freeze-dry product of Limulus Amebocyte Lysate were mixed, the mixture was put into the piezoelectric crystal cell and immediately thereafter, the deficit resistance and the change of the resonant frequency were measured continuously. The relationship between the time and the deficit resistance and between the time and the resonant frequency change measured for a sample containing 10 pg/ml of endotoxin by a 9 MHz AT cut piezoelectric crystal are shown in FIGS. 8A and 8B, respectively. It could be understood from FIG. 8A that the viscosity increased with the gelation reaction and became constant with the end of the gelation reaction. FIG. 9 shows the relationship between the endotoxin concentration and the gelation time, and demonstrates that the measuring system of the present invention can detect the endotoxin concentration.

Figure 10:
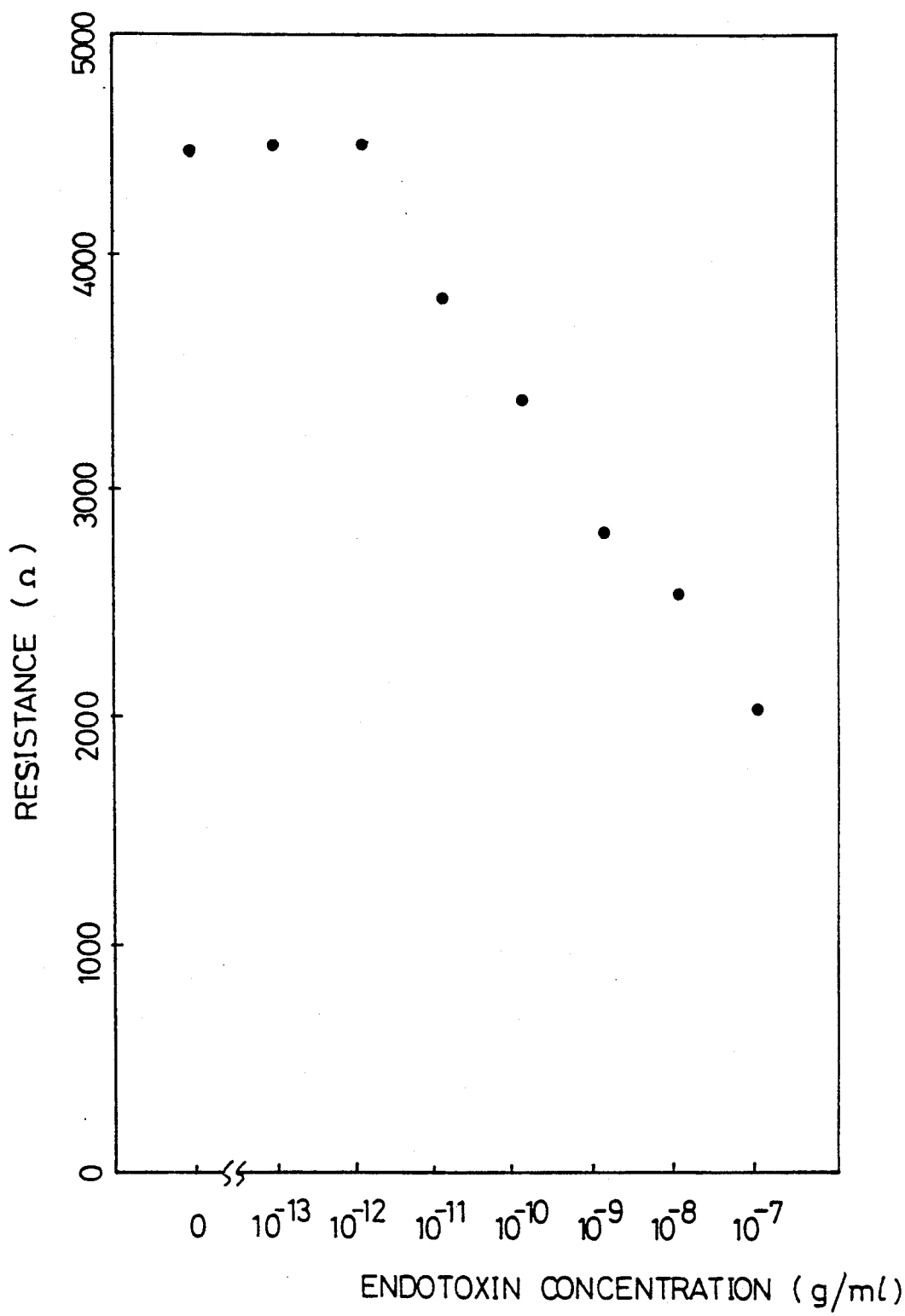
FIG. 10 shows the value of the deficit resistance after the gelation with respect to the endotoxin concentration.

In addition to the viscosity change, the system of the present invention can be used for measuring the adsorption reaction. This was demonstrated by the fact that adsorption of albmin to the piezoelectric crystal from an aqueous albmin solution could be traced from the continuous change of the resonant frequency. Therefore, if the adsorption reaction and the gelation reaction occur simultaneously, the rate of the gelation reaction can be estimated not only from the gelation time but also from the value of the deficit resistance and the change of the resonant frequency after the end of gelation. The adsorption reaction proceeds simultaneously in the measurement of endotoxin, too, and FIG. 10 shows the value of the deficit resistance after the end of gelation with respect to the endotoxin concentration.

EXAMPLE 5

The viscosity measuring system by the present example is used as a gelation detector.

The gelation reaction measuring system in accordance with the present example places a piezoelectric crystal on the bottom of a well type cell, places a sample solution into the cell and determines the gelation time from the change of the oscillation frequency of the piezoelectric crystal. Furthermore, the frequency change at the time of gelation reaction is amplified by adding solid fine particles into the sample solution The present example comprises at least an oscillation circuit, a frequency measuring device and a data processing unit in addition to a piezoelectric resonator.

The piezoelectric crystal is a device which utilizes a piezoelectric property. When connected to an oscillation circuit, the piezoelectric crystal causes oscillation. At this time, the surface of the piezoelectric crystal causes vibration. Therefore, if any material comes into contact with the surface, influences are exerted to this vibration and are reflected as the change of the oscillation frequency.

Accordingly, if the change of the oscillation frequency with the gelation reaction is measured, the oscillation frequency changes with the progress of the reaction and the end of the change is observed with the completion of the gelation reaction. The gelation time can be measured by measuring the change of this oscillation frequency.

Furthermore, if solid fine particles are suspended in the sample, the fine particles settle to the surface of the piezoelectric crystal at the stage where gelation has not yet been complete and the oscillation frequency changes. When the gelation is complete, however, the fine particles are entrapped in the gel so that the change of the oscillation frequency due to sedimentation of the fine particles stops. In consequence, the frequency change at the time of the gelation reaction can be amplified.

Figure 11:
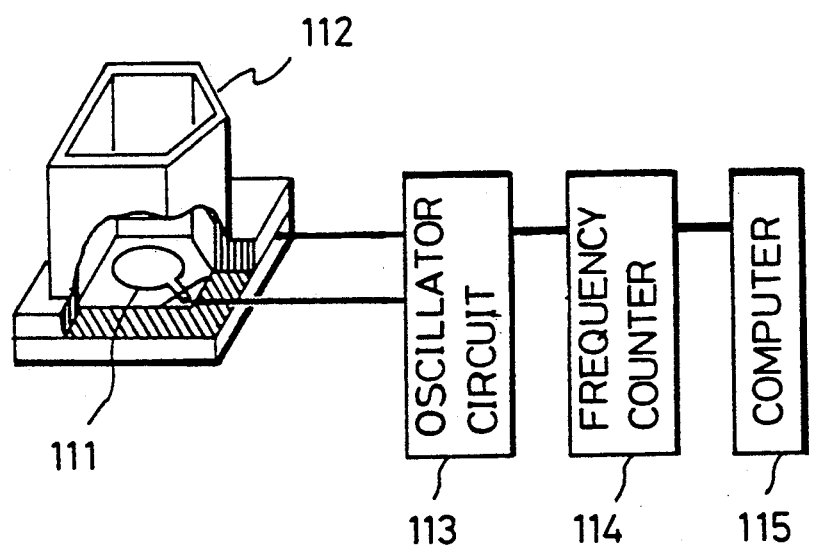
FIG. 11 is a schematic view of a gelation reaction measuring system in accordance with the present invention.

The viscosity measuring system used in the present example is shown in FIG. 11.

In FIG. 11, an AT cut piezoelectric resonator 111 is fixed to a cell 112 which is arranged in such a manner that the piezoelectric resonator serves as its bottom surface, and is connected to an oscillation circuit 113. The oscillation circuit is connected to a frequency counter 114, which is in turn connected to a computer 115 for monitoring and calculating data.

Application to determination of fibrinogen concentration

Figure 12:
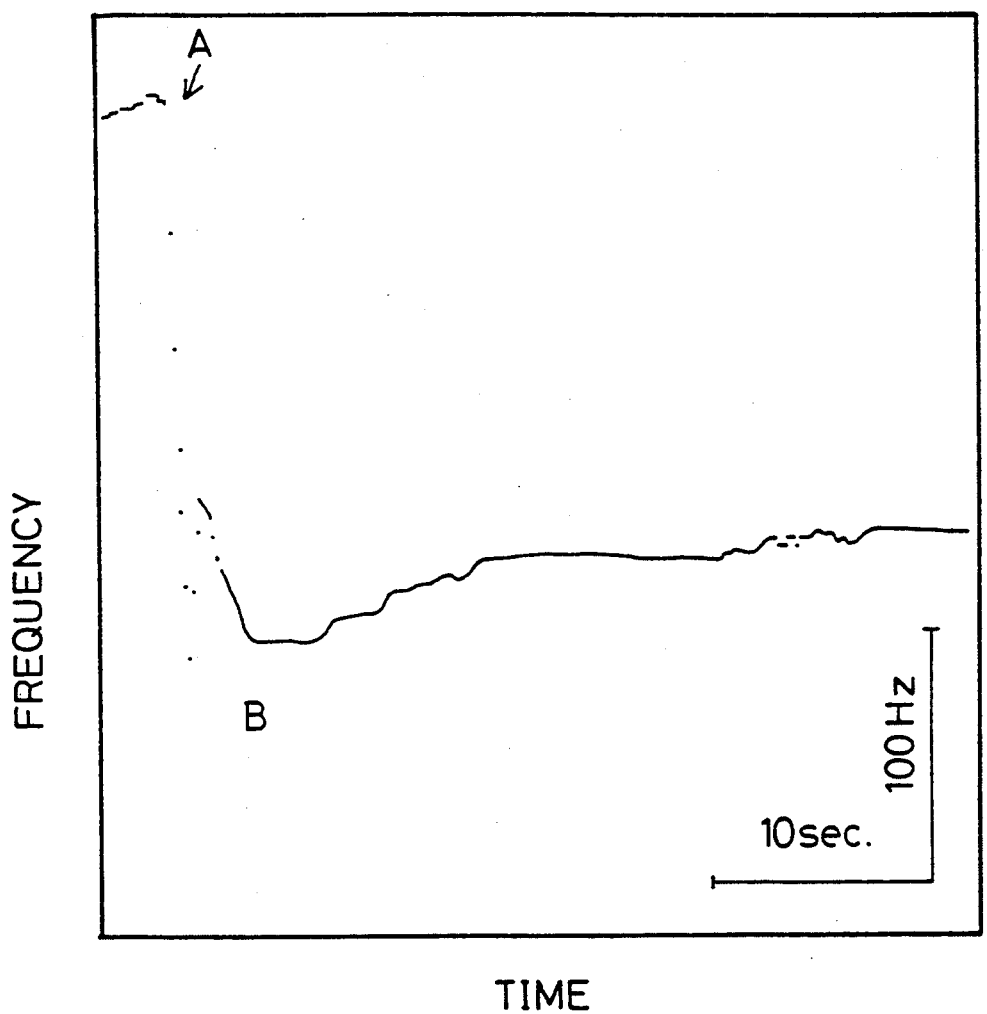
FIG. 12 is a diagram showing the change of an oscillator frequency at the time of the gelation reaction of fibrinogen.

The fibrinogen concentration was measured in the following way. First, a 20 NIH/ml of an aqueous thrombin solution(0.2 ml, 20° C.) containing 8 $\mu$g/ml of polybrene was prepared and mixed with 0.2 ml of an aqueous fibrinogen solution that had in advance been put into the cell and incubated at 37° C. FIG. 12 shows the result of measurement of the change of the oscillation frequency at this time with respect to 500 mg/dl of fibrinogen. In FIG. 12, the point A indicates the time at which the aqueous thrombin solution was mixed and the point B indicates the point where gelation was complete, and the oscillation frequency became constant. The time difference between these points A and B was calculated automatically by the computer to obtain the gelation time.

Figure 13:
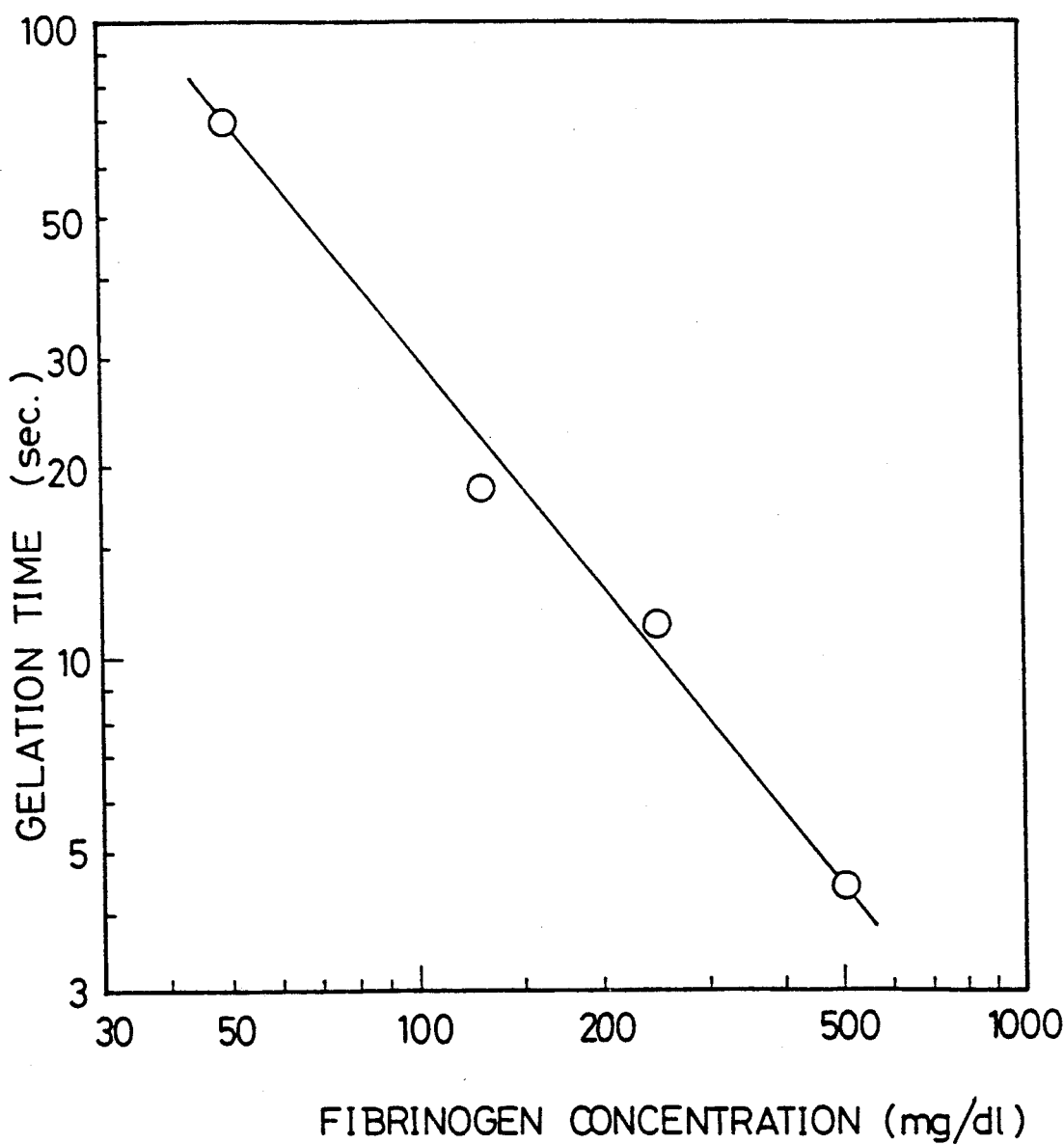
FIG. 13 is a diagram showing the relationship between a fibrinogen concentration and a gelation time.

FIG. 13 shows the result of the study on the correlation between the fibrinogen concentration and the gelation time by adding alumina particles (diameter 5 $\mu$m, 1 wt%). It can be seen from FIG. 13 that they have a substantially linear relationship and are in good agreement with the result obtained by the conventional measurement method. The measurement was similarly possible when $\mu$m alumina particles were used. The measurement could be carried out also satisfactorily when the amount of the alumina particles was below 10 wt%. The measurement by the addition of the alumina particles was extremely effective in the aspect of covering the influences of the temperature change of the system.

Furthermore, the measurement using the measuring system of the present invention has the characterizing feature in that the measurement is possible even when the sample quantity is as small as only 20 $\mu$l. The gelation reaction measuring system of the present invention can measure the gelation reaction and the gelation reaction time accurately and even with a trace amount of a sample.

What is claimed is:

1. A method for analyzing a gelation reaction by utilizing a viscosity measuring system comprised of a piezoelectric resonator for detecting the viscosity of liquid, the gelation reaction being a reaction involving a viscoelastic change, the method comprising the steps of:
   (a) contacting the piezoelectric resonator with the liquid;

(b) adding said particles into the liquid to amplify a variation of a resonator characteristic which varies in accordance with gelation of the liquid; and (c) monitoring the resonant frequency shift indicating the shift from resonant frequency measured in air while allowing the gelation reaction to proceed.

2. A method according to claim 1, further comprising the step of determining a concentration of the chemical substance in the liquid according to the reaction end time based on a calibration curve obtained previously.

3. A method according to claim 1, wherein the solid particles are alumina particles.

4. A method according to claim 1; wherein the contacting step comprises contacting the piezoelectric resonator with a liquid comprised of a mixture of aqueous thrombin solution and aqueous fibrinogen solution to thereby enable a determination of fibrinogen concentration by gelating with thrombin.

5. A method according to claim 1; wherein the contacting step comprises contacting the piezoelectric resonator with a liquid comprised of a mixture of limulus amebocyte lysate and endotoxin to thereby enable a determination of endotoxin concentration by gelation of limulus amebocyte lysate.

6. A method for analyzing a chemical reaction by utilizing a viscosity measuring system comprised of a piezoelectric resonator for detecting the viscosity of liquid, the chemical reaction being a reaction involving a viscoelastic change, the method comprising the steps of:

(a) contacting the piezoelectric resonator with the liquid;

(b) adding solid particles into the liquid to amplify a variation of a resonator characteristic which varies in accordance with gelation of the liquid; and (c) monitoring a resistance change in an electrical equivalent circuit of the piezoelectric resonator while allowing the chemical reaction to proceed.

7. A viscosity measuring system comprising:

a sensor comprised of a piezoelectric resonator for detecting the viscosity of liquid;

measuring means coupled to the piezoelectric resonator for measuring an index of the viscosity of the liquid by monitoring characteristics of the piezoelectric resonator; and a cell for holding therein the liquid, the piezoelectric resonator being mounted at the bottom of the cell so that only one side of the piezoelectric resonator comes in contact with the liquid, and the liquid having solid particles suspended therein for determining gelation time of the liquid by monitoring the stop of sedimentation of the particles on the piezoelectric resonator.

8. A viscosity measuring system according to claim 7, wherein the measuring means comprises means for measuring the index of the viscosity of the liquid in terms of the resonant frequency shift of the piezoelectric resonator.

9. A viscosity measuring system according to claim 8; wherein the measuring means comprises a resonator frequency measuring circuit for measuring the resonant frequency of the piezoelectric resonator.

10. A viscosity measuring system according to claim 8, wherein the measuring means comprises an impedance analyzer, and resonant frequency calculating unit.

11. A viscosity measuring system according to claim 7; wherein the measuring means comprises means for measuring the index of the viscosity of the liquid in terms of the resistance of the piezoelectric resonator, the resistance being defined as a resistance component in an equivalent circuit of the resonator comprised of a capacitance, an inductance and a resistance in series with one another.

12. A viscosity measuring system according to claim 11; wherein the measuring means comprises a resistance measuring circuit for measuring the resistance of the piezoelectric resonator.

13. A viscosity measuring system according to claim 11; wherein the measuring means comprises an impedance analyzer, and a resonant frequency calculating unit.

14. A viscosity measuring system according to claim 11; wherein the measuring means comprises an oscillator circuit, and a frequency measuring device.

15. A viscosity measuring system according to claim 7; wherein the solid particles comprise alumina particles present in an amount effective to prevent inaccurate measurement due to temperature changes in the liquid.

16. A gelation reaction measuring system, comprising: a cell containing gelable liquid; a piezoelectric resonator mounted in the cell at the bottom thereof so that only one side of the piezoelectric resonator comes in contact with the liquid, the piezoelectric resonator having a prescribed characteristic which varies in accordance with the gelating of the liquid; solid particles suspended in the liquid and depositable on the piezoelectric resonator during gelating of the liquid to amplify the variation of the resonator characteristic; and measuring means coupled to the piezoelectric resonator for measuring the variation of the resonator characteristic to determine the gelation time of the liquid.

17. A system according to claim 16; wherein the measuring means comprises means for measuring the index of the viscosity of the liquid in terms of the resonant frequency shift of the piezoelectric resonator.

18. A system according to claim 16; wherein the measuring means comprises a resonator frequency measuring circuit for measuring the resonant frequency of the piezoelectric resonator.

19. A system according to claim 16, wherein the measuring means comprises an impedance analyzer, and a resonant frequency calculating unit.

20. A system according to claim 16; wherein the measuring means comprises a resistance measuring circuit for measuring the resistance of the piezoelectric resonantor.

21. A system according to claim 16; wherein the measuring means comprises an oscillator circuit, and a frequency measuring device.

* * * * *